United States Patent [19]

Oediger et al.

[11] 4,447,367

[45] May 8, 1984

[54] PHOSPHONOFORMALDEHYDE, A PROCESS FOR ITS PREPARATION AND ITS USE AS AN INTERMEDIATE PRODUCT FOR THE PREPARATION OF MEDICAMENTS

[75] Inventors: Hermann Oediger, Cologne; Folker Lieb, Leverkusen; Hans Disselnkötter, Cologne, all of Fed. Rep. of Germany

[73] Assignee: Bayer Aktiengesellschaft, Leverkusen, Fed. Rep. of Germany

[21] Appl. No.: 370,890

[22] Filed: Apr. 22, 1982

Related U.S. Application Data

[62] Division of Ser. No. 308,717, Oct. 5, 1981, Pat. No. 4,348,332.

[30] Foreign Application Priority Data

Oct. 23, 1980 [DE] Fed. Rep. of Germany ....... 3039998

[51] Int. Cl.³ .............................................. C07F 9/38
[52] U.S. Cl. ............................................. 260/502.4 R
[58] Field of Search ................................. 260/502.4 R

[56] References Cited

PUBLICATIONS

Morita et al., "Bull Chem. Soc. Japan," vol. 51, (7), (1978), pp. 2169–2170.

*Primary Examiner*—J. E. Evans
*Attorney, Agent, or Firm*—Sprung, Horn, Kramer & Woods

[57] ABSTRACT

The invention relates to phosphonoformaldehyde of the formula

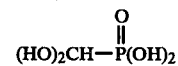

Also included in the invention is a method for the manufacture of said phosphonoformaldehyde in which a dialkoxymethane phosphonic acid is warmed with water (then reacted with a base if a salt is desired.) Phosphonoformaldehyde is an intermediate for the manufacture of phosphonohydroxy acetic acid, which is an antiviral agent.

2 Claims, No Drawings

PHOSPHONOFORMALDEHYDE, A PROCESS FOR ITS PREPARATION AND ITS USE AS AN INTERMEDIATE PRODUCT FOR THE PREPARATION OF MEDICAMENTS

This is a division, of application Ser. No. 308,717, filed Oct. 5, 1981 now U.S. Pat. No. 4,348,332.

The present invention relates to a certain new phosphorus compound and to an unobvious process for its production. The compound can be used as an intermediate product for the synthesis of pharmaceuticals.

Formylphosphonic acid esters have already been disclosed (see U.S. Pat. No. 3,784,590). However, as investigations carried out by the applicants have shown, they are very unstable and are therefore not particularly suitable as intermediate products for industrial syntheses.

Dimethoxymethanephosphonic acid in the form of the monoanilinium salt has also been disclosed (see Bull. Chem. Soc. Japan 51 (1978), 2169).

According to the present invention there is provided the compound phosphonoformaldehyde of the formula $$(HO)_2CH-\overset{\overset{O}{\|}}{P}(OH)_2 \quad (I)$$

or a salt thereof.

The compound of the invention finds particular use in the synthesis of an antiviral agent for use in medicine.

According to the present invention there is further provided a process for the production of a compound of the invention in which a dialkoxymethanephosphonic acid of the formula $$(RO)_2CH-\overset{\overset{O}{\|}}{P}(OH)_2 \quad (II)$$

in which both radicals R represent an alkyl group with 1 to 4 carbon atoms, is warmed with water and, if it is desired to convert the free phosphonoformaldehyde into a salt thereof, is then reacted with a base.

The phosphonoformaldehyde according to the invention can subsequently be converted into salts by conventional methods.

If, in the reaction, dimethoxymethanephosphonic acid is used as the starting substance and sodium hydroxide solution is used for the neutralisation, the course of the reaction is illustrated by the following equation:

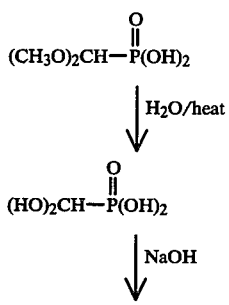

$(HO)_2CH-\overset{\overset{O}{\|}}{P}(ONa)_2$

The dialkoxymethanephosphonic acids used as starting substances for the process according to the invention are known (see Bull. Chem. Soc. Japan 51 (1978), 2169), or they can be prepared by known processes.

In the formula (II), the two radicals R preferably represent, as the alkyl group with 1 to 4 carbon atoms, a methyl or ethyl group.

Compounds of formula (II) which may be mentioned are, for example, dimethoxymethanephosphonic acid, diethoxymethanephosphonic acid and dipropoxymethanephosphonic acid.

It is not necessary to add the starting materials as such. It is sufficient to use aqueous solutions of these compounds, such as are formed in situ when the corresponding trimethylsilyl esters are hydrolysed with water.

Moreover, it is also not necessary to purify the trimethylsilyl esters used, but it is sufficient for the trimethylsilyl esters such as are formed when dialkoxymethanephosphonic acid dialkyl esters are reacted with for example, trimethylbromosilane to be hydrolysed, without further purification. The process is thus particularly economical.

When warming the compounds of the formula (II) in water in order to carry out the process according to the present invention generally a temperature in the range from $+70°$ to $+100°$ C., preferably between $+80°$ and $+90°$ C., is used.

The reaction time depends on the temperature and on the structure of the radical R, and is generally between 1 hour and 3 hours.

The resulting compound of formula (I) can be isolated either by evaporating the solution or, for isolation in the form of a phosphonic acid salt, after adding to the solution an amount of an inorganic or organic base, for example an inorganic base such as an alkali metal hydroxide, which is sufficient for neutralisation of the solution, for example by adding aqueous sodium hydroxide solution. Suitable organic bases are, for example, pyridine and triethylamine.

It is indeed known to convert aldehyde acetals into the free aldehydes with strong acids, for example hydrochloric acid, sulphuric acid or phosphoric acid. For this conversion, for example in the case of aliphatic aldehyde acetals, relatively large amounts of acid and elevated temperatures are required (see Vogel, Text-Book of Organic Chemistry, 3rd Edition, Page 323, Longmans, London).

However, it is to be described as surprising that the acidity of the compounds of formula (II) is sufficient to prepare the compound of formula (I), which is in the form of the hydrate and is therefore unusually stable, without the addition of foreign acids.

It is exceptionally advantageous that the addition of foreign acids can be dispensed with, since isolation of the aldehyde, for example as the phosphonic acid salt, is thus particularly simple.

The process can be carried out as a one-pot reaction, starting from the dialkoxymethanephosphonic acid alkyl ester, in a particularly economical manner if the stoichiometrically required amount of, for example, trimethylbromosilane is used to prepare the starting compound of the general formula (II).

Phosphonoformaldehyde is an intermediate product for the preparation of medicaments, in particular for the preparation of phosphonohydroxyacetic acid, which has antiviral properties.

For example, phosphonoformaldehyde of formula (I) in the form of its sodium salt reacts with hydrocyanic acid to give the new compound phosphonohydroxyacetonitrile of formula (III), which can be converted into phosphonohydroxyacetic acid of formula (IV) by hydrolysis of the nitrile group, for example with hydrochloric acid.

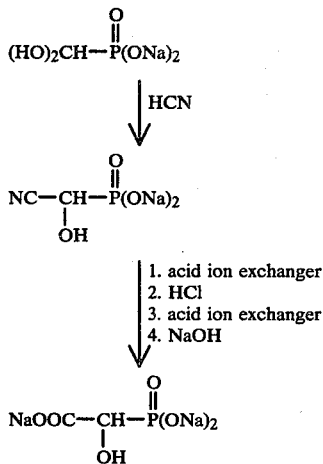

Phosphonohydroxyacetic acid has an action against herpes viruses in warm-blooded animals, in particular against type I and II herpes simplex viruses.

The process for the production of phosphonohydroxyacetonitrile according to the present invention is illustrated by the following Examples.

EXAMPLE 1

Na$_2$ salt of phosphonoformaldehyde 184 g (1 mole) of dimethoxymethanephosphonic acid dimethyl ester were dissolved in 800 ml of acetonitrile, 366 g (2.4 moles) of trimethylbromosilane were added at +15° to +20° C. and the mixture was then stirred at +40° to +45° C. for 2 hours. The solvent and the excess trimethylbromosilane were removed at +30° to +40° C. in vacuo, the evaporation residue was dissolved in 600 ml of water, hexamethyldisiloxane and methanol were then distilled off at a temperature rising to about +80° C., the water which was also distilled off being continuously replaced, and the mixture was then stirred for a further hour at 80° to 85° C. The mixture was cooled, adjusted to a pH value of about 7.5 with 3 N NaOH and evaporated in vacuo and the crystalline residue was dried in vacuo.

170 g (89% of theory) of the dihydrate of the Na$_2$ salt of phosphonoformaldehyde were obtained in this manner.

$^1$H-NMR: $\delta = 4.9$ (1H, d, J=4.0 Hz) ppm (D$_2$O)

$^{13}$C-NMR: $\delta = 90$ (d, J$_{C,P}$=180.7 Hz) ppm (D$_2$O)

Phosphonoformaldehyde can be converted into phosphonohydroxyacetic acid in the following manner:

(a) The Na$_2$ salt of phosphonohydroxyacetonitrile 15 g (0.083 mole) of the dihydrate of the Na$_2$ salt of phosphonoformaldehyde were suspended in 30 ml of H$_2$O, and 10 ml of anhydrous hydrocyanic acid were then added at about +25° C. The temperature rose to +30° C.; a clear solution was formed. The mixture was kept for a further hour at +30° C., the excess hydrocyanic acid and the water were then removed in vacuo and the residue was dried in vacuo.

15 g (95% of theory) of the dihydrate of the Na$_2$ salt of phosphonohydroxyacetonitrile were obtained in this manner.

$^1$H-NMR: $\delta = 4.5$ (1H,d,J=16.0 Hz) ppm (D$_2$O)

$^{13}$C-NMR: $\delta = 122.3$ (C$\equiv$N); 60.2 (d, J$_{C,P}$=133.3 Hz) ppm (D$_2$O)

(b) The Na$_3$ salt of phosphonohydroxyacetic acid 9.5 g (0.05 mole) of the dihydrate of the Na$_2$ salt of phosphonohydroxyacetonitrile were converted into phosphonohydroxyacetonitrile on an acid ion exchanger, the phosphonohydroxyacetonitrile was dissolved in 30 ml of concentrated hydrochloric acid and the solution was left to stand overnight. It was warmed for a further 4 hours to 85° to 90° C., the solvent was removed in vacuo, the evaporation residue was taken up in water and the solution was filtered over an acid ion exchanger. The filtrate was evaporated in vacuo, the solution obtained by dilution with water was adjusted to a pH value of about 7.5 and the water was removed in vacuo. 8.3 g (75% of theory) of the Na$_3$ salt of phosphonohydroxyacetic acid were obtained in this manner.

$^1$H-NMR: $\delta = 4.1$ (1H, d, J=18 Hz) ppm (D$_2$O)

$^{13}$C-NMR: $\delta = 168.1$ (COO$^\ominus$); 73.7 (d, J$_{C,P}$=134.1) ppm (D$_2$O)

EXAMPLE 2

306 g (2 moles) of trimethylbromosilane were added to 184 g (1 mole) of dimethoxymethanephosphonic acid dimethyl ester at +15° to +20° C. and the mixture was then stirred at +40° to +45° C. for 2 hours. 600 ml of water were then added at +10° to +20° C. and the procedure followed was as described in Example 1. 173 g (19% of theory) of the dihydrate of the Na$_2$ salt of phosphonoformaldehyde were obtained.

EXAMPLE 3

12.0 g (0.05 mole) of diethoxymethanephosphonic acid diethyl ester were dissolved in 40 ml of acetonitrile, 18.3 g (0.12 mole) of trimethylbromosilane were added at +15° to +20° C. and the mixture was then stirred at +45° to +50° C. for 2 hours. The procedure followed was then as described in Example 1, but the mixture was adjusted to a pH value of about 7.5 with 2 N LiOH. 6.3 g (90% of theory) of the hydrate of the Li$_2$ salt of phosphonoformaldehyde were obtained in this manner.

EXAMPLE 4

9.2 g (0.05 mole) of dimethoxymethanephosphonic acid dimethyl ester were dissolved in 40 ml of acetonitrile, 18.3 g (0.12 mole) of trimethylbromosilane were added to +15° to +20° C. and the mixture was then stirred at +45° to +50° C. for two hours. The procedure followed was then as described in Example 1, but one equivalent of pyridine was added. 9.3 g (90% of theory) of the hydrate of the monopyridinium salt of phosphonoformaldehyde were obtained in this manner.

Melting point: 156° to 158° C. (decomposition).

What is claimed is:

1. A process for the production of the compound of the formula

which comprises warming a dialkoxymethanephosphonic acid of the formula

in which
both radicals R represent an alkyl group with 1 to 4 carbon atoms, with water to a temperature in the range from $+70°$ to $+100°$ C., and if it is desired to convert the free phosphonoformaldehyde into a salt thereof, reacting the free phosphonoformaldehyde with a base.

2. A process according to claim 1, in which both radicals R represent a methyl or ethyl group.

* * * * *